United States Patent
Vigil et al.

[11] Patent Number: 5,713,863
[45] Date of Patent: Feb. 3, 1998

[54] CATHETER WITH FLUID MEDICATION INJECTORS

[75] Inventors: Dennis M. Vigil, San Diego, Calif.; Peter L. Barath, Hinsdale, Ill.

[73] Assignee: InterVentional Technologies Inc., San Diego, Calif.

[21] Appl. No.: 584,310

[22] Filed: Jan. 11, 1996

[51] Int. Cl.$^6$ ............................................. A61M 29/00
[52] U.S. Cl. ............... 604/104; 604/53; 604/105; 604/183; 606/198
[58] Field of Search ................. 604/19, 22, 48–50, 604/52, 53, 93, 104–9, 181, 183, 264; 606/191, 198

[56] References Cited

U.S. PATENT DOCUMENTS

| | | |
|---|---|---|
| 3,593,713 | 7/1971 | Bogoff . |
| 3,635,223 | 1/1972 | Klieman . |
| 4,465,072 | 8/1984 | Taheri . |
| 4,922,926 | 5/1990 | Hirschberg et al. ............... 604/93 |
| 5,009,659 | 4/1991 | Hamlin et al. . |
| 5,030,201 | 7/1991 | Palestrant ............... 604/22 |
| 5,112,305 | 5/1992 | Barath et al. . |
| 5,242,397 | 9/1993 | Barath et al. ............... 604/96 |
| 5,279,565 | 1/1994 | Klein et al. ............... 606/198 |
| 5,282,785 | 2/1994 | Shapland et al. . |
| 5,286,254 | 2/1994 | Shapland et al. . |
| 5,295,962 | 3/1994 | Crocker et al. . |
| 5,306,250 | 4/1994 | March et al. ............... 604/104 |
| 5,336,178 | 8/1994 | Kaplan et al. . |
| 5,354,279 | 10/1994 | Hofling . |
| 5,364,356 | 11/1994 | Hofling . |
| 5,423,851 | 6/1995 | Samuels ............... 606/198 |
| 5,571,086 | 11/1996 | Kaplan et al. ............... 604/96 |
| 5,599,306 | 2/1997 | Klein et al. ............... 604/53 |
| 5,609,574 | 3/1997 | Kaplan et al. ............... 604/53 |

FOREIGN PATENT DOCUMENTS

| | | |
|---|---|---|
| 0 399 712 | 11/1990 | European Pat. Off. . |
| 0 567 788 A1 | 3/1993 | European Pat. Off. . |
| WO 94/23787 | 10/1994 | WIPO . |

*Primary Examiner*—Michael Powell Buiz
*Assistant Examiner*—Bhisma Mehta
*Attorney, Agent, or Firm*—Nydegger & Associates

[57] ABSTRACT

A device for injecting medication into a vessel wall includes a plurality of flexible tubes mounted between a multi-lumen catheter and a grommet. A push-pull wire is connected to the grommet and passed through a lumen of the multi-lumen catheter. A plurality of injectors are mounted on each of the flexible tubes. During use, the device is first positioned in a vessel. The push-pull wire is then partially withdrawn forcing the grommet to advance towards the multi-lumen catheter. The advancing grommet forces the flexible tubes to bow outwardly, embedding the injectors into the vessel wall. A fluid medication is then introduced through the multi-lumen catheter, into the flexible tubes and out of the injectors for infusion into the vessel wall.

18 Claims, 3 Drawing Sheets

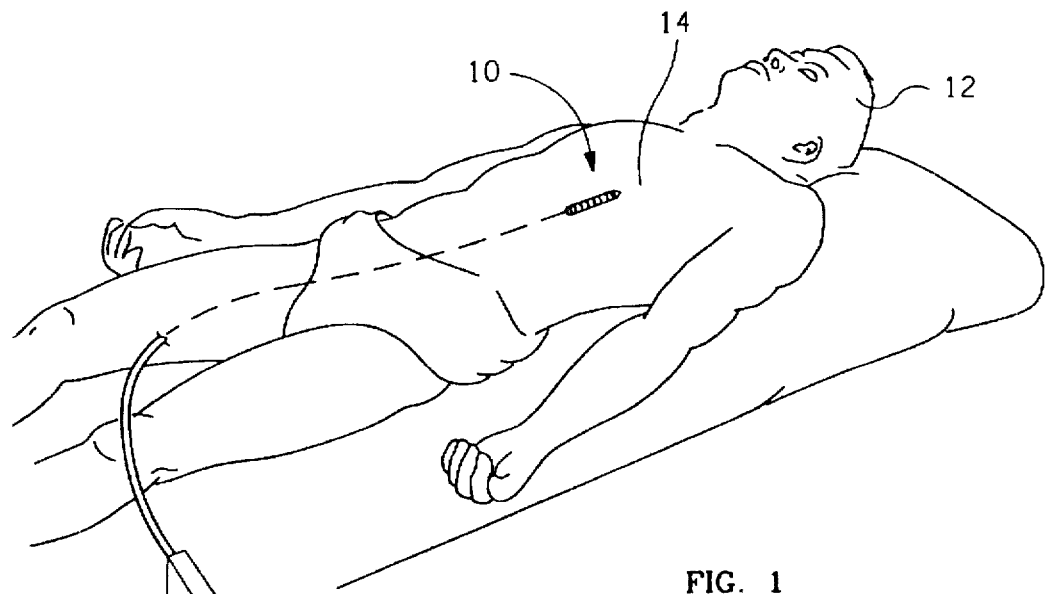
FIG. 1
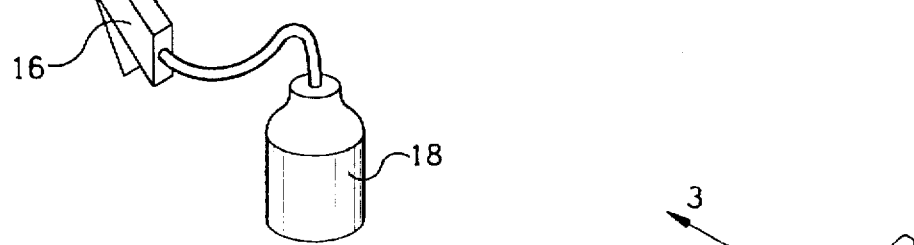
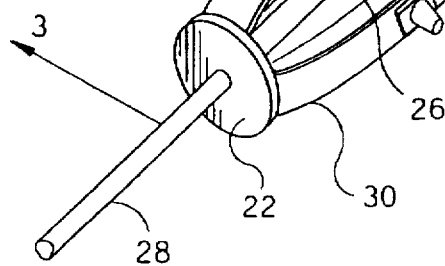
FIG. 2

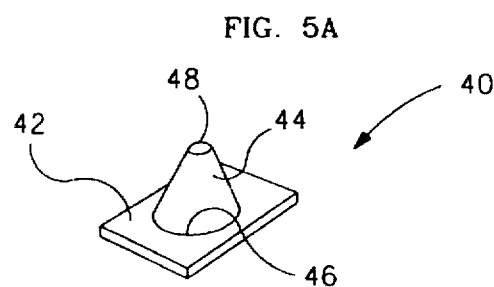
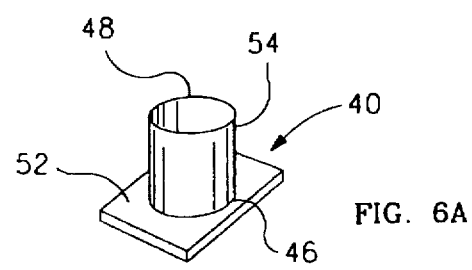
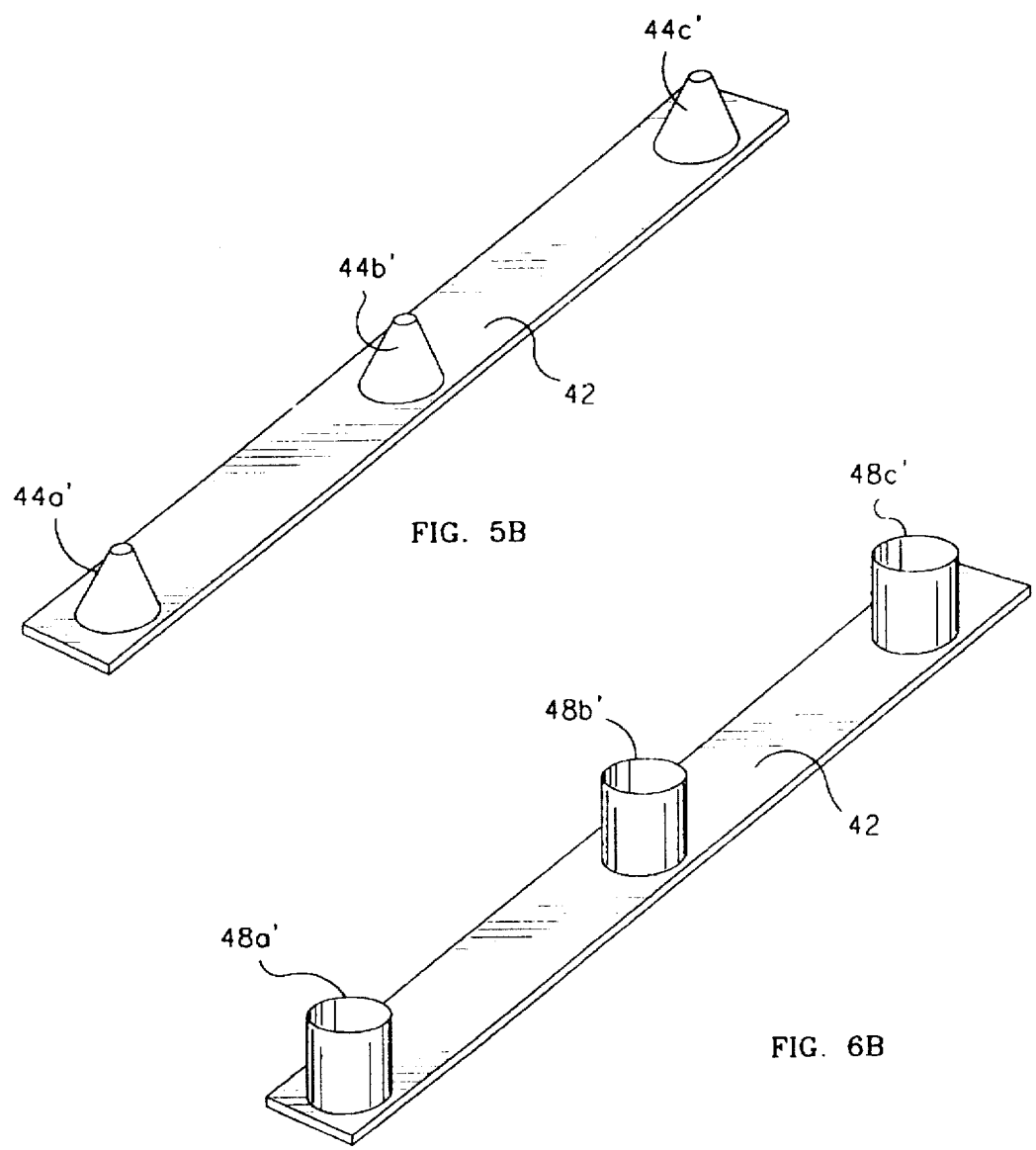
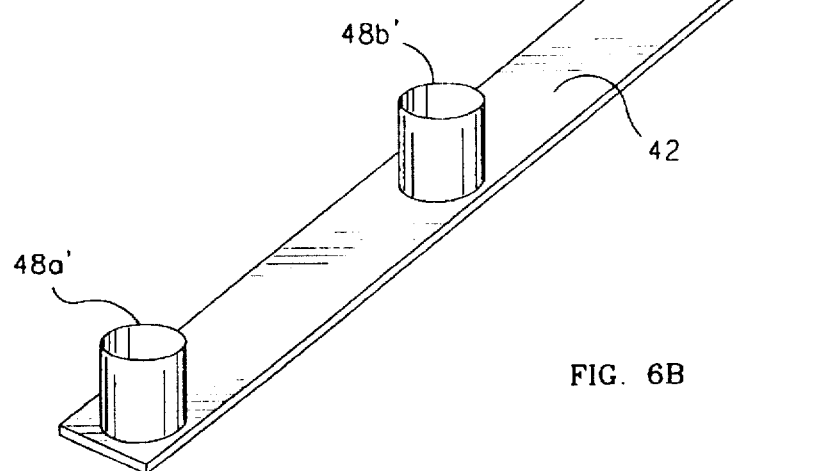

CATHETER WITH FLUID MEDICATION INJECTORS

FIELD OF THE INVENTION

The present invention pertains generally to invasive medical devices which are useful for the purpose of infusing fluid medicaments into a patient. More specifically, the present invention pertains to medical devices which can be inserted into a vessel of a patient's cardiovascular system. The present invention is particularly, but not exclusively, useful for infusing fluid medicaments directly into a vessel wall.

BACKGROUND OF THE INVENTION

Depending on the particular ailment it is known in the medical field that fluid medications can be infused directly into the wall of a vessel of a patient's cardiovascular system with beneficial results. For example, one such application involves the administration of medicaments into an arterial wall which will inhibit or prevent the restenosis of plaque in the artery following an angioplasty procedure. Any procedure involving the direct infusion of fluid medicaments into a vessel wall, however, requires the consideration of several factors. First, the procedure must be safe. For instance, due to the toxic nature of some medicaments, such a procedure must insure that only minimal amounts of medication are ever washed away into the blood stream and not actually infused into the vessel wall. Second, the device which infuses the medication into the vessel wall must be easy to use, accurate in its delivery capability and reliable in its operation.

Several devices have been suggested for the purpose of infusing fluid medicaments directly into a vessel wall. One example of such a device is disclosed in U.S. Pat. No. 5,354,279 which issued to Hofling for an invention entitled "Plural Needle Injection Catheter." The specific device disclosed in this patent includes a catheter having a plurality of longitudinally oriented channels. A hollow needle is disposed longitudinally in each of the channels. In use, the hollow needles are advanced distally with respect to the catheter. As the needles advance, the special shape of the channels forces the needles to bend outward, extending the needles radially to penetrate the vessel wall. The extended needles are then used for infusion of the fluid medicament.

In general, it should be appreciated that several operational disadvantages are associated with the longitudinal arrangement of the channels and needles of the device disclosed in this patent. Specifically, it should be appreciated that the inclusion of the plurality of needles oriented longitudinally within the catheter has the effect of creating a relatively stiff catheter which may be unsuitable for many applications. Additionally, it should be appreciated that the complexity of routing the needles and channels through the catheter effectively limits devices of this type to a relatively small number of needles. In many applications, of course, a large number of infusion needles will be more appropriate.

U.S. Pat. No. 5,364,356, was issued to Hofling for another invention entitled "Sleeve Catheter." This second patent to Hofling discloses a device which employs a balloon expandable sleeve that delivers fluid medication to a vessel wall. More specifically, this device of Hofling's includes a reconfigurable sleeve which is expanded by an inflatable balloon. It is intended that, as the sleeve expands, openings which are formed into the sleeve spread to discharge fluid medications onto the surface of the vessel walls. Structurally, the second Hofling patent provides an infusion device which does not require internal routing of longitudinally oriented infusion needles. As a result, the second Hofling device may be used in combination with a highly flexible placement catheter. Unfortunately, the lack of infusion needles in the second Hofling device has the result that injection of medication directly into the vessel wall is impossible. Direct injection will, in some cases, be required for effective treatment.

Still another example of a device for medicating a vessel wall is disclosed in U.S. Pat. No. 5,112,305 which issued to Barath et al. for an invention entitled "Catheter Device for Intramural Delivery of Therapeutic Agents." This same device is also disclosed in a related U.S. Pat. No. 5,242,397 which issued to Barath et al. for an invention entitled "Catheter Device and Method of Use for Intramural Delivery of Protein Kinase C and Tyrosine Protein Kinase Inhibitors to Prevent Restenosis after Balloon Angioplasty." Specifically, the device disclosed by Barath et al. employs a balloon which requires an initial slow filling of the balloon with a medicament to expand the balloon and position the balloon's surface against the vessel wall. This initial slow filling is then followed by a rapid filling of the balloon which reconfigures tubular extensions on the surface of the balloon for the infusion of medicaments through the tubular extensions and into the vessel wall. Importantly, in the device of Barath et al., a single, pressurized, source of fluid medicament is used for infusion, and for expansion of the device. It may be appreciated, however, that there are cases where the pressure required to inflate the device of Barath et al. may be greater or lesser than the optimal infusion pressure. As a result, while the device of Barath et al. is generally effective, there may be cases where treatment may be enhanced if the infusion pressure may be controlled independently from the pressure required to expand the device and penetrate the vessel wall.

The present invention recognizes that it is preferable to have a mechanism for infusing medication into a vessel wall which includes a relatively large number of infusion needles. The present invention also recognizes that it is preferable to have a mechanism for infusing medication into a vessel wall which may be positioned using a highly flexible placement catheter. Additionally, the present invention recognizes that it is preferable to have an apparatus wherein the mechanism used for perforation of the vessel wall is separated from the mechanism used for subsequent infusion. Further, the present invention recognizes that, depending on the nature and condition of the vessel wall, it is preferable to have the capability of selectively applying a variable force to the injectors of the device as they penetrate into the vessel wall.

In light of the above, it is an object of the present invention to provide a device for injecting medication into the wall of a vessel which includes a mechanism for penetrating a vessel wall with medication delivery injectors that is separate from the mechanism which infuses the medication into the vessel wall. Another object of the present invention is to provide a device for injecting medication into the wall of a vessel which may be used with a relatively flexible placement catheter. Yet another object of the present invention is to provide a device for injecting medication into the wall of a vessel which provides a relatively large number of injectors. It is another object of the present invention to provide a device for injecting medication into the wall of a vessel which can selectively vary the force that is used to penetrate the vessel wall with a fluid medication injector. Still another object of the present invention is to provide a device for injecting medication into the wall of a vessel which is easy to use, relatively simple to manufacture and comparatively cost effective.

SUMMARY OF THE PREFERRED EMBODIMENTS

In accordance with the present invention, a device for injecting medication into the wall of a vessel includes a multi-lumen catheter and a grommet. The catheter and the grommet are both disposed about the same longitudinal axis with the grommet separated distally from the distal end of the multi-lumen catheter. Importantly, the grommet is movable in translation along the longitudinal axis to allow the separation between the grommet and the multi-lumen catheter to either increase or decrease.

The present invention also includes a plurality of hollow, flexible, tubes which are each formed with a lumen and which each have a distal end, a central region, and a proximal end. The distal end of each of the tubes is attached to the grommet. The proximal end of each of the tubes is attached to the catheter. The attachment between the tubes and the catheter, as well as the attachment between the tubes and the grommet, arranges the plurality of tubes radially around the catheter. In this arrangement, the attachment between the multi-lumen catheter and the plurality of tubes is such that the lumen of each tube is connected in fluid communication with a respective lumen of the multi-lumen catheter. As a result, fluid may be supplied under pressure to pass through the multi-lumen catheter and into the plurality of tubes. In general, each tube is connected to an individual lumen within the catheter. Alternatively, the plurality of tubes may be connected singly, or in combination, to one or more common lumens within the multi-lumen catheter.

A plurality of injectors are attached to the central region of each flexible tube to project radially outward from the longitudinal axis of the present invention. Each injector is shaped conically or cylindrically and defines a channel which is in fluid communication with the lumen of the flexible tube to which the injector is attached. As a result, fluid which is passed through the multi-lumen catheter and into the lumens of the flexible tubes also passes through the channel and out of the injectors.

A push-pull wire is connected to the grommet and passed through one of the lumens of the multi-lumen catheter. The insertion of the push-pull wire through the multi-lumen catheter allows the push-pull wire to be moved translationally along the longitudinal axis of the present invention. Furthermore, the translational movement of the push-pull wire causes the grommet to move translationally with respect to the multi-lumen catheter. In this fashion, the push-pull wire may be used to increase, or decrease, the separation between the grommet and the multi-lumen catheter.

As can be easily appreciated, any translational movement of the grommet, caused by the push-pull wire, is accommodated by the flexible tubes. More specifically, as the separation between the grommet and the multi-lumen catheter decreases, each of the flexible tubes arches, or bows, outwardly, from the longitudinal axis giving the device an expanded configuration. Alternatively, as the push-pull wire is advanced to increase the separation between the grommet and the multi-lumen catheter, each of the flexible tubes straightens, or flattens, giving the device a contracted configuration.

In the operation of the device of the present invention, a guidewire is first positioned into an artery of the patient. This is done to establish a mechanical pathway through the artery to the site where the fluid medication is to be infused. The extracorporeal end of the guidewire is then inserted into a lumen of the multi-lumen catheter and the multi-lumen catheter is advanced over the guidewire until the injectors on the flexible tube are adjacent to the site where the medication is to be infused.

Once the device has been properly positioned, the push-pull wire is partially withdrawn from the multi-lumen catheter. Withdrawal of the push-pull wire decreases the separation between the grommet and the multi-lumen catheter causing each of the tubes to bow outward away from the longitudinal axis and towards the arterial wall. This action also causes the injectors to penetrate into the arterial wall. The fluid pump is then activated to inject fluid from the fluid source, or sources, through the multi-lumen catheter, into the flexible tubes, and out of the injectors, thereby infusing the arterial wall. Simultaneous infusion of separate medications may be accomplished by passing the different medications through separate lumens within the multi-lumen catheter to emerge through separate tubes and injectors.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 1 is a perspective view of the device of the present invention shown operationally positioned within a patient for the infusion of medication into a vessel wall;

FIG. 2 is a perspective view of the device of the present invention;

FIG. 5A is a perspective view of the single port injector of the present invention;

FIG. 5B is a perspective view of the multi-port injector of the present invention;

FIG. 6A is a perspective view of an alternative embodiment of the single port injector of the present invention;

FIG. 6B is a perspective view of an alternative embodiment of the multi-port injector of the present invention.

DESCRIPTION OF THE PREFERRED EMBODIMENT

Figure 3:
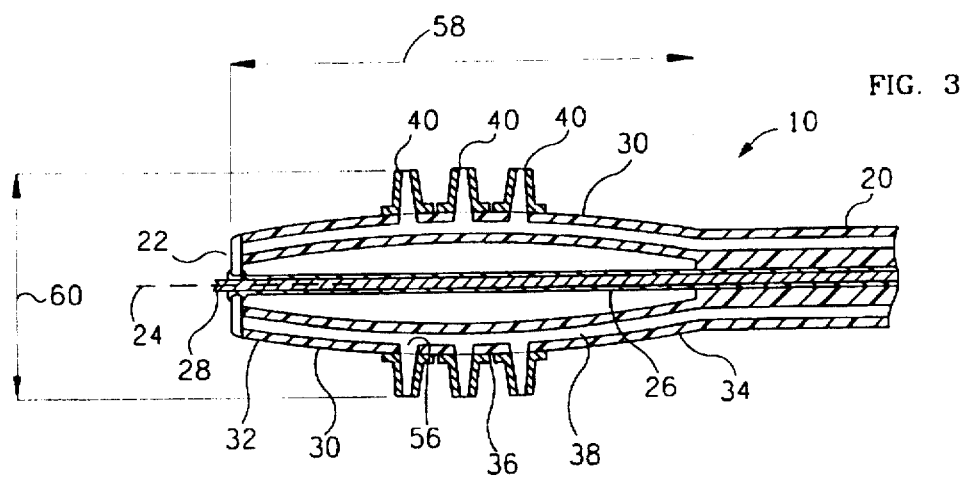
FIG. 3 is a cross-sectional view of the device of the present invention shown in the retracted configuration as seen along the line 3—3 in FIG. 2.

Referring initially to FIG. 1, a device for injecting fluid medication into the wall of a vessel in accordance with the present invention is shown and generally designated 10. For purposes of illustration, the device 10 is shown in an operational position after being advanced through the femoral artery and toward the heart 14 of the patient 12. It is to be appreciated, however, that the device 10 is useful in vessels throughout the vascular system of patient 12 and may be introduced into the vessel wherever it is most convenient to do so. FIG. 1 also shows that the device 10 is connected to a control unit 16 which selectively controls the application of a source of fluid medication 18.

The structural details of the present invention are appreciated more easily by initial reference to FIG. 2 where it may be seen that the device 10 includes a multi-lumen catheter 20 and a grommet 22. Both the multi-lumen catheter 20 and the grommet 22 are disposed about the same longitudinal axis 24 with the grommet 22 positioned distally, and separated from, the distal end of the multi-lumen catheter 20.

The present invention also includes some type of apparatus which can be used to move the grommet 22 translationally along the longitudinal axis 24. For example, in the device shown in FIG. 2, a push-pull wire 26, is shown connected to the grommet 22. The push-pull wire 26 extends through one of the lumens of the multi-lumen catheter 20 allowing the push-pull wire 26 to move translationally in line with the longitudinal axis 24. The translational movement of the push-pull wire 26 causes the grommet 22 to undergo a similar translational displacement. In many cases, it will be desirable to use the device 10 of the present invention in combination with a guidewire 28. In such cases, the push-pull wire 26 may be formed with an internal lumen through which the guidewire 28 may be passed.

A plurality of hollow, flexible tubes 30 are attached between the grommet 22 and the multi-lumen catheter 20. In greater detail, each of the flexible tubes 30 may be seen to include a distal end 32, a proximal end 34 and a central region 36. The proximal end 34 of each tube 30 is joined to the multi-lumen catheter 20. The distal end 32 of each tube 30 is joined to the grommet 22. Preferably, the tubes 30 are distributed radially around the multi-lumen catheter 20 and grommet 22 in a manner substantially as shown in FIG. 2.

Figure 4:
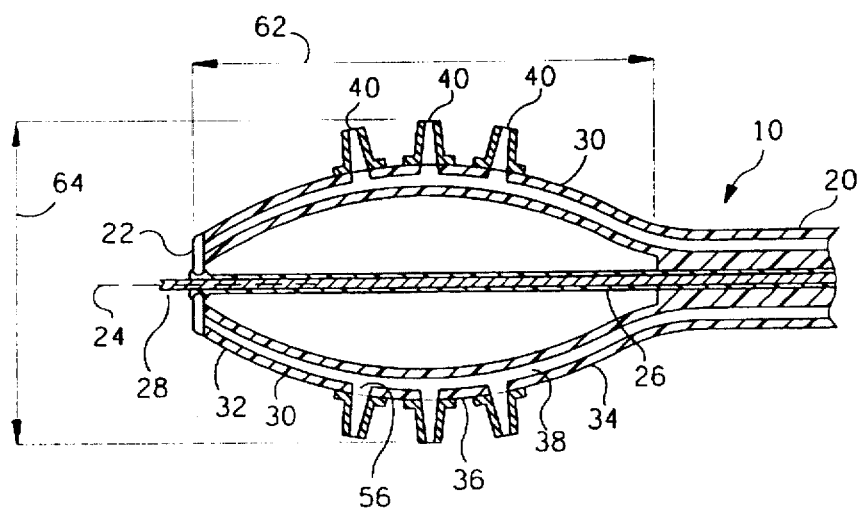
FIG. 4 is a cross-sectional view of the device of the present invention as seen in FIG. 3, with the device now shown in the expanded configuration.

Turning now to FIGS. 3 and 4, it may be seen that each flexible tube 30 is formed with a lumen 38. FIG. 3 and 4 also show that the lumen 38 of flexible tubes 30 passes through flexible catheter 20 allowing fluid medication to be passed through multi-lumen catheter 20 and into flexible tubes 30. Specifically, the fluid pump 16 of FIG. 1 may be used to pass fluid medication from the fluid source 18 into the multi-lumen catheter 20 and into flexible tubes 30. As shown in FIGS. 3 and 4, the lumen 38 of each flexible tube 30 passes separately through multi-lumen catheter 20 allowing a different medication to be passed into each flexible tube 30. Alternatively, the lumen 38 of each flexible tube 30 may be attached to one or more common lumens within multi-lumen catheter 20.

FIG. 3 and 4 also show that a plurality of injectors 40 are attached to the central region 36 of each of the flexible tube 30. The structural details of the injectors 40 may be seen more clearly in FIG. 5A where an injector 40 is shown to include a base plate 42 and a conically shaped, hollow protrusion 44 which projects therefrom. Further, it is seen that the end 46 of protrusion 44 is affixed to or integral with the base plate 42. Preferably, the injector 40 is made of nickel and the protrusion 44 is formed by punching out the base plate 42. In any event, a cutting edge 48 is formed around the end of protrusion 44 that is opposite from the end 46 on plate 42 and the resultant structure establishes a fluid channel which extends through the injector 40.

In FIG. 6A, another embodiment for an injector of the present invention is shown and designated 52. Rather than having a conically shaped protrusion 44 like the injector 40, however, the injector 52 has a substantially cylindrically shaped protrusion 54. Like injector 40, the injector 52 is preferably made of nickel and is formed to have a fluid channel which extends through the injector 52.

For a multi-port injector version of the present invention, a plurality of protrusions 44 can be formed from the same base plate. FIG. 5B shows such an embodiment. Specifically, FIG. 5B shows an elongated base plate 42 from which the protrusions 44a', 44b' and 44c' have been formed. In all important respects, the protrusions 44' shown in FIG. 5B are structurally the same as the protrusion 44 discussed above with reference to FIG. 5A. The only difference being that they are collectively mounted on the same base plate 42.

Similarly, FIG. 6B shows a multi-port injector wherein the protrusion 48a', 48b' and 48c' have been formed from a base 42. In all important respects, the protrusions 48a', 48b' and 48c' shown in FIG. 6B are structurally the same as the protrusion 54 discussed above with reference to FIG. 6A. Again, the only difference being that they are collectively mounted on the same base plate 42.

Returning to FIGS. 3 and 4, it may be seen that each flexible tube 30 is formed with a plurality of holes 56 which correspond to a respective injector 40. Functionally, each hole 56 connects the channel of a respective injector 40 to lumen 38 allowing the fluid pump 16 of FIG. 1 to pump medication from the fluid source 18 into lumen 38 to be expelled through the injector 40.

FIGS. 3 and 4 also show that the present invention is movable between a contracted configuration (shown in FIG. 3) and an expanded configuration (shown in FIG. 4). In greater detail, it may be seen that the grommet 22 and the multi-lumen catheter are distanced by a first separation 58. The device 10 shown in FIG. 3 also has a first overall width designated 60. In comparison, the grommet 22 and the multi-lumen catheter 20, shown in FIG. 4 are distanced by a second separation 62 which is smaller than the first separation 58 of FIG. 3. The device 10 shown in FIG. 4 also has a second overall width 64 which is greater than the first overall width 60 shown in FIG. 3.

The difference between the contracted configuration shown in FIG. 3 and the expanded configuration shown in FIG. 4 is accomplished, of course, by translational movement of the grommet 22 along the longitudinal axis 24. In more detail, it may be appreciated that as the push-pull wire 26 causes the grommet 22 to move towards the multi-lumen catheter 20, each of the flexible tubes 30 bows outwardly away from the longitudinal axis 24. In this fashion, the push-pull wire 26 may be used to move the grommet 22 translationally to cause the flexible tubes to alternately bow, as seen in FIG. 4, and straighten, as seen in FIG. 3. In some cases, it will be preferable to fabricate the flexible tubes 30 from resilient material which biases the tubes 30 into either the bowed or straight configuration.

Figure 7:
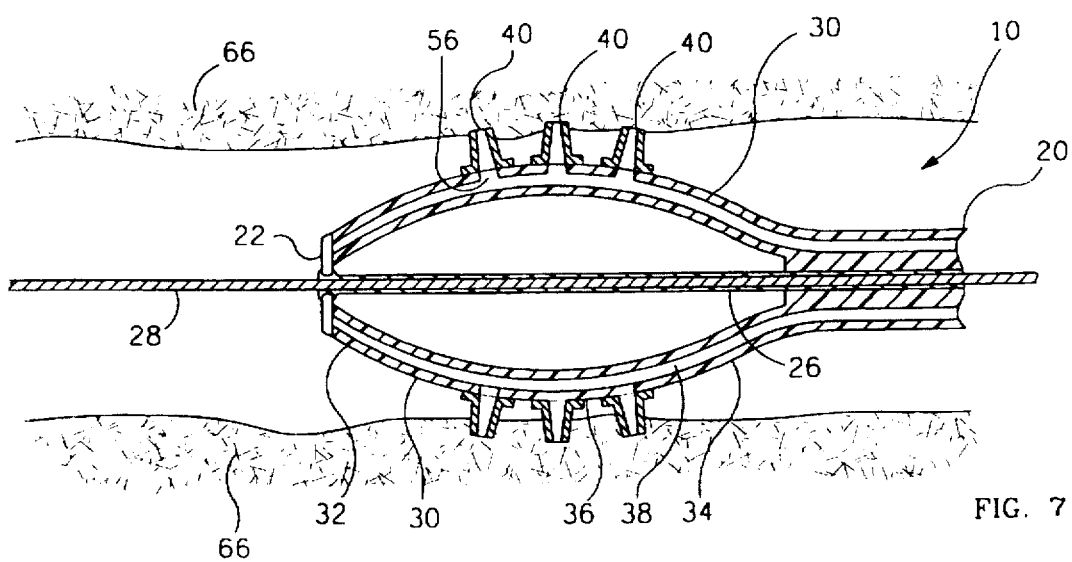
FIG. 7 is a cross-sectional view of the device of the present invention as seen in FIG. 3, with the device now shown operationally positioned within the vessel of a patient.

A typical operation sequence for the present invention, as best appreciated by reference to FIG. 7, begins with insertion of the guidewire 28 into the vessel of a patient. More specifically, the guidewire 28 is first positioned in the vessel to establish a mechanical path for the device 10 to the site, where fluid medications are to be infused into a vessel wall 66. Once the guidewire 28 is properly positioned, the extracorporeal end of the guidewire is threaded through the lumen of the push-pull wire 26 and through the multi-lumen catheter 20. The device 10 of the present invention is then advanced over the guidewire 28 until the injectors 40 are adjacent to the target site where fluid medications are to be infused into the vessel wall 66.

Once the device 10 is properly positioned, the push-pull wire 26 is partially withdrawn from the multi-lumen catheter 20. As indicated above, withdrawal of the push-pull wire 26 decreases the separation between the grommet 22 and the distal end of the multi-lumen catheter 20, causing the tubes 30 to bow towards the vessel wall 66. The bowing tubes 30 force the injectors 40 to first contact and then pierce the vessel wall 66.

With the injectors 40 embedded into the vessel wall 66, the control unit 16 shown in FIG. 1 is activated to pump fluid from the fluid source 18, through the multi-lumen catheter 20, into the lumen 38 of the flexible tubes 30 to be expelled at injectors 40 infusing the vessel wall 66. After the fluid medication has been infused into the vessel wall 66, the push-pull wire 26 is advanced into the multi-lumen catheter 20. The advancing push-pull wire increases the separation between the grommet 22 and the distal end of the multi-lumen catheter 20 causing each of the tubes 30 to straighten along longitudinal axis 24. The straightening tubes 30 cause the injectors 40 to be withdrawn from the vessel wall 66. The entire device 10 can then be withdrawn from the patient 12 over the guidewire 28.

While the particular device for injecting medication into the wall of a vessel as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A device useful for infusing a medicament into an arterial wall which comprises:

a catheter defining a longitudinal axis;

a grommet disposed about said longitudinal axis;

a plurality of resilient tubes, each said tube formed with a tube lumen and having a proximal end, a distal end, and a central region, said proximal end of each said tube being attached to said catheter and said distal end of each said tube being attached to said grommet;

at least one hollow injector attached to and projecting away from said central region of each said tube, said hollow injector being in fluid communication with said tube lumen;

means for moving said grommet along said longitudinal axis between a first position wherein said central region of each said tube is held substantially juxtaposed to said longitudinal axis with said injector projecting away from each said tubes and a second position wherein said central region of each said tube is radially distanced from said longitudinal axis to urge said hollow injector into an arterial wall; and means in fluid communication with each said tube lumen adapted for injecting a medicament into each said tube lumen and through said injectors.

2. A device as recited in claim 1 wherein said injectors comprise:

a base; and a hollow protrusion having a first end and a second end, said protrusion projecting from said base to establish a fluid channel through said base and through said protrusion, said first end of said protrusion being affixed to said base and said second end formed with a cutting edge.

3. A device as recited in claim 2 wherein said protrusions are substantially cylindrical in shape.

4. A device as recited in claim 2 wherein said protrusions are substantially conical in shape.

5. A device as recited in claim 1 wherein said catheter is formed with at least one catheter lumen.

6. A device as recited in claim 5 wherein one said catheter lumen is attached in fluid communication with each said tube lumen.

7. A device as recited in claim 5 wherein one said catheter lumen is dimensioned to receive a guidewire therethrough and positioning said device.

8. A device as recited in claim 7 wherein said means for moving said grommet comprises a push-pull wire, said push-pull wire being attached to said grommet and extending through one said catheter lumen.

9. A device useful for infusing a medicament into an arterial wall which comprises:

a catheter defining a longitudinal axis;

a grommet disposed about said longitudinal axis;

a plurality of resilient tubes, each said tube having a proximal end, a distal end, and a central region, said proximal end of each said tube being attached to said catheter, said distal end of each said tube attached to said grommet;

at least one injector attached to and projecting away from said central region of each said tube;

means for moving said central region of each said tube between a first position wherein said central region is held substantially juxtaposed to said longitudinal axis with said injector projecting away from each said tube and a second position wherein said central region is radially distanced from the longitudinal axis to urge said hollow injector into an arterial wall; and pumping means in fluid communication with each said injector which is adapted for injecting a medicament through the injectors.

10. A device as recited in claim 9 wherein said injectors comprise:

a base; and a hollow protrusion having a first end and a second end, said protrusion projecting from said base to establish a fluid channel through said base and through said protrusion, said first end of said protrusion being affixed to said base and said second end formed with a cutting edge.

11. A device as recited in claim 10 wherein said protrusions are substantially cylindrical in shape.

12. A device as recited in claim 10 wherein said protrusions are substantially conical in shape.

13. A device as recited in claim 10 wherein said catheter is formed with at least one catheter lumen.

14. A device as recited in claim 13 wherein one said catheter lumen is attached in fluid communication with said tube.

15. A device as recited in claim 13 wherein one said catheter lumen is dimensioned to receive a guidewire therethrough for guiding and position said device.

16. A device as recited in claim 15 wherein said means for moving said central region of each said tube comprises a push-pull wire, said push-pull wire attached to said grommet and extending through one said lumen of said catheter.

17. A method for infusing a medicament into an arterial wall which comprises the steps of:

advancing a device through the vessel, said device comprising a catheter defining a longitudinal axis, a grommet disposed about said longitudinal axis, a plurality of resilient tubes, each said tube having a proximal end, a distal end, and a central region, said proximal end of each said tube being attached to said catheter, said distal end of each said tube attached to said grommet, at least one hollow injector attached to and projecting away from said central region of each said tube, a push-pull wire for moving said central region of each said tube between a first position wherein said central region is held substantially juxtaposed to said longitudinal axis with said injector projecting away from each said tube and a second position wherein said central region is radially distanced from said longitudinal axis to urge said hollow injector into the arterial wall, and means in fluid communication with each said hollow injector for injecting a medicament through said hollow injectors into the arterial wall;

selectively withdrawing said push-pull wire to move said central region of each said tube to said second position to urge said hollow injectors into the arterial wall; and selectively activating said pumping means to pass a medicament through said injectors to infuse the vessel wall.

18. A method as recited in claim 17 further comprising the steps of:

prepositioning a guidewire in the vessel;

positioning a catheter lumen of the device over a portion of the guidewire; and advancing said device over said guidewire.

* * * * *